US006214768B1

(12) United States Patent
Castro et al.

(10) Patent No.: US 6,214,768 B1
(45) Date of Patent: Apr. 10, 2001

(54) SYNERGISTIC HERBICIDAL METHODS AND COMPOSITIONS

(75) Inventors: Kelly Neoob DeCarvalao Castro, Rio De Janeiro (BR); Timothy Malefyt, Yardley, PA (US); Robert M. Watkins, Starkville, MS (US); Wilson Mendonca, Rio de Janeiro (BR); Frederick P. Salzman, Lawrenceville, NJ (US)

(73) Assignee: American Cyanamid Co., Madison, NJ (US)

( * ) Notice: Subject to any disclaimer, the term of this patent is extended or adjusted under 35 U.S.C. 154(b) by 0 days.

(21) Appl. No.: 09/396,173

(22) Filed: Sep. 14, 1999

Related U.S. Application Data

(60) Provisional application No. 60/100,093, filed on Sep. 14, 1998.

(51) Int. Cl.$^7$ ............................................. A01N 57/00
(52) U.S. Cl. ................................................. 504/128
(58) Field of Search ........................................ 504/128

(56) References Cited

U.S. PATENT DOCUMENTS

| 4,440,562 | * | 4/1984 | Prill ............................. 71/86 |
| 4,816,060 |   | 3/1989 | Steller et al. ............... 71/92 |
| 4,822,405 | * | 4/1989 | Martin et al. ............... 71/92 |
| 5,206,021 |   | 4/1993 | Dookhith et al. ........... 424/405 |
| 5,478,795 |   | 12/1995 | Watkins, Jr. ................ 504/130 |
| 5,563,112 | * | 10/1996 | Barnes, III .................. 504/125 |
| 5,597,778 |   | 1/1997 | Smale ......................... 504/127 |
| 5,672,617 |   | 9/1997 | Wachtler et al. ........... 514/407 |

FOREIGN PATENT DOCUMENTS

| 220 902 A2 | 5/1987 | (EP) | ............................... A01N/57/20 |
| 256 414 A2 | 2/1988 | (EP) | ............................... A01N/25/22 |
| 433 577 A1 | 6/1991 | (EP) | ............................... A01N/25/04 |
| 2233229 | 1/1991 | (GB) | ............................... A01N/57/20 |
| 9608148 | * 3/1996 | (WO) | ............................... A01N/41/10 |

OTHER PUBLICATIONS

Bruff et al., "Tank–mix combinations for weed control in stale seedbed soybean (*Glycine max*)", Weed Technology, 6(1), pp. 45–51 (1992).
Lanie et al., "Herbicide Combinations for Soybean (*Glycine max*) Planted in Stale SeedBed", Weed Technology, 8(1), pp. 17–22 (1994).
CA124: 281878 abstract of Sanders et al., "Control of nut grass (*Cyperus rotundus*) in asparagus", Proc N. Z. Plant Prot. Conf., 48$^{th}$, pp. 322–326 (1995).
Lanie et al, Herbicide Combinations for Soybean Planted in Slate Seedbed, Weed Technology, vol. 8, pp. 17–22, 1994.*

* cited by examiner

*Primary Examiner*—Jose' G. Dees
*Assistant Examiner*—Alton Pryor
(74) *Attorney, Agent, or Firm*—John W. Hogan, Jr.; Barbara V. Maurer

(57) ABSTRACT

The present invention provides a method for the synergistic control of undesirable plants such as Ipomoea, Cyperus, Sida and Euphorbia which comprises applying to the plants or their locus a synergistically effective amount of a combination of glyphosate and an imidazolinone compound. Further provided are synergistic herbicidal compositions comprising glyphosate and an imidazolinone compound, and specifically concentrated aqueous herbicidal compositions of imidazolinyl acid salts and glyphosate salts.

14 Claims, No Drawings

SYNERGISTIC HERBICIDAL METHODS AND COMPOSITIONS

This application claims priority from copending provisional application Ser. No. 60/100,093 filed on Sep. 14, 1998.

BACKGROUND OF THE INVENTION

Certain weeds such as Ipomoea, Cyperus, Sida and Euphorbia are particularly difficult to control. Their full-season competition can reduce crop yields and cause significant economic loss in row-crop production. One of the most common practices for controlling these troublesome weeds is the postemergent application of a herbicide. However, there is no single selective herbicide currently available which will give economic control of these weeds.

Glyphosate [(N-phosphonomethyl)glycine] is a highly effective herbicide with a broad spectrum of activity. However, certain agronomically important weed species require relatively high application rates of glyphosate for effective control. High rates of glyphosate can lead to undesirable increased selection pressure. Glyphosate tolerance, particularly in Ipomoea, is a recognized problem in the field. Therefore, new weed control methods and compositions which effectively lower glyphosate application rates while providing broad spectrum weed control are highly desirable.

Aqueous compositions containing imidazolinyl acid salts are described in U.S. Pat. No. 4,816,060, and aqueous compositions containing glyphosate salts are described in EP 220,902-A2. However, concentrated, aqueous compositions comprising an imidazolinyl acid salt and a glyphosate salt have not been described. The principal reason that aqueous compositions containing both of those compounds have not been disclosed is that imidazolinyl acid salts and glyphosate salts are, in general, not mutually compatible. Aqueous glyphosate salt compositions generally have a pH value of about 4. However, imidazolinyl acid salts are not entirely stable in an environment having a pH value of about 4. Conversely, glyphosate salts are not entirely stable at the pH values required to provide stable aqueous compositions of imidazolinyl acid salts.

To overcome the incompatibility problems associated with aqueous compositions containing imidazolinyl acid salts and glyphosate salts, emulsifiable suspension concentrate compositions containing imidazolinyl acids and glyphosate have been described (see, e.g., U.S. Pat. No. 5,268,352). However, emulsifiable suspension concentrate compositions are not entirety satisfactory because they require the use of heavy aromatic solvents.

What is needed in the art is an aqueous composition which overcomes the incompatibility problems associated with imidazolinyl acid salts and glyphosate salts without requiring the use of heavy aromatic solvents.

SUMMARY OF THE INVENTION

Surprisingly, it has now been found that the combination of glyphosate with an imidazolinone compound provides synergistic weed control. Advantageously, the synergistic combination of the invention allows for lower application rates of glyphosate with concomittant increased spectrum of weed control. Moreover, the synergistic herbicidal methods and compositions of the invention allow for effective resistance management programs and provide improved control of pestiferous weeds such as Ipomoea in glyphosate-resistant crop production.

The present invention provides a method for the synergistic control of undesirable plants such as Ipomoea, Cyperus, Sida or Euphorbia which comprises applying to the locus of said plants or to the foliage or stems of said plants a synergistically effective amount of a combination of glyphosate and at least one imidazolinone compound selected from the group consisting of imazethapyr, the R isomer thereof or a salt thereof; imazaquin, the R isomer thereof or a salt thereof; imazapic, the R isomer thereof or a salt thereof; imazamox, the R isomer thereof or a salt thereof; imazapyr, the R isomer thereof or a salt thereof; and mixtures thereof.

The present invention also relates to a concentrated, aqueous herbicidal composition which comprises about 0.1% w/v to about 7% w/v of an imidazolinyl acid salt, about 10% w/v to about 45% w/v of a glyphosate salt, about 0.5% w/v to about 6% w/v of dimethyl sulfoxide, about 0.5% w/v to about 15% w/v of a wetting agent, up to about 10% w/v of an antifreezing agent, up to about 1% w/v of an anti-foaming agent, up to about 5% w/v of a base, and water, provided that the composition has an initial pH of from about 6.0 to about 7.2.

Preferred concentrated, aqueous herbicidal compositions of this invention comprise about 0.1% w/v to about 7% w/v of an imidazolinyl acid salt, about 15% w/v to about 45% w/v of a glyphosate salt, about 0.5% w/v to about 6% w/v of dimethyl sulfoxide, about 0.5% w/v to about 15% w/v of a wetting agent, up to about 10% w/v of an antifreezing agent, up to about 1% w/v of an anti-foaming agent, up to about 3% w/v of a base, and water, provided that the composition has an initial pH of from about 6.0 to about 7.0.

The present invention further relates to a process or the preparation of the concentrated, aqueous herbicidal compositions of this invention.

DETAILED DESCRIPTION OF THE INVENTION

Glyphosate [(N-phosphonomethyl)glycine] is a highly effective broad spectrum herbicide. However, certain troublesome weeds such as Ipomoea, Sida, Cyperus and Euphorbia may require very high application rates of glyphosate for effective control. High application rates of glyphosate may decrease the margin of crop safety, increase the potential development of weed tolerance and result in the loss of economic weed control.

Surprisingly, it has now been found that the application of a combination of glyphosate plus at least one imidazolinone compound selected from imazethapyr, the R isomer thereof or a salt thereof; imazaquin, the R isomer thereof or a salt thereof; imazamox, the R isomer thereof or a salt thereof; imazapic, the R isomer thereof or a salt thereof; and imazapyr, the R isomer thereof or a salt thereof provides synergistic control of troublesome weeds, particularly Ipomoea, Sida, Cyperus and Euphorbia, especially Ipomoea. That is, the application of the combination of the invention gives a mutual reinforcing action such that the application rates of the individual herbicidal components can be reduced and still the same herbicidal effect is achieved or, alternatively, the application of the combination of herbicidal components demonstrates a greater herbicidal effect than expected from the effect of the application of the individual herbicidal components when applied singly (synergistic effect).

As used in the specification and claims, the term glyphosate designates the compound N-(phosphonomethyl)-glycine or the agriculturally acceptable salts thereof.

Similarly, the terms used for the imidazolinone compounds imazethapyr, imazaquin, imazapic, imazamox and imazapyr as they appear in the specification and claims designate the compound, the R isomer thereof, an agriculturally acceptable salt thereof or mixtures thereof unless the context clearly dictates otherwise. The imidazolinone compounds and their corresponding chemical names are listed herein below.

Imazethapyr designates 5-ethyl-2-(4-isopropyl-4-methyl-5-oxo-2-imidazolin-2-yl)nicotinic acid, the R isomer thereof, a salt thereof, or mixtures thereof.

Imazaquin designates 2-(4-isopropyl-4-methyl-5-oxo-2-imidazolin-2-yl)quinolinecarboxylic acid, the R isomer thereof, a salt thereof, or mixtures thereof.

Imazapic designates 2-(4-isopropyl-5-methyl-5-oxo-2-imidazolin-2-yl)-5-methylnicotinic acid, the R isomer thereof, a salt thereof, or mixtures thereof.

Imazamox designates 2-(4-isopropyl-4-methyl-5-oxo-2-imidazolin-2-yl)-5-(methoxymethyl)nicotinic acid, the R isomer thereof, a salt thereof, or mixtures thereof.

Imazapyr designates 2-(4-isopropyl-4-methyl-5-oxo-2-imidazolin-2-yl)nicotinic acid, the R isomer thereof, a salt thereof, or mixtures thereof.

In the context of the present invention, the term agriculturally acceptable salt includes alkali metal, ammonium, alkyl sulphonium or alkylphosphonium salt or the quatenary salt of an amine having a molecular weight of less than 300. In particular, the term includes isopropylammonium, ammonium, sodium and trimesium, especially isopropylammonium and ammonium.

As used in the specification and claims, the term R isomer designates the optical isomer of an imidazolinone compound having the R configuration assigned to the assymetric carbon in the imidazolinone ring which is substituted by a methyl and an isopropyl group, for example the R isomer of the imidazolinone compound imazapyr is shown below.

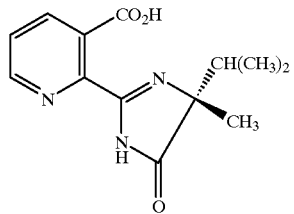

In general, commercial formulations of glyphosate are aqueous solutions of an agriculturally acceptable salt such as glyphosate-isopropylammonium, glyphosate-sesquisodium, glyphosate trimesium and the like. Similarly, imidazolinone herbicides and their agriculturally acceptable salts are commercially available as aqueous solutions. Additionally, imidazolinone herbicides are commercially available as dispersible granules, soluble granules and the like. In actual practice, the combination of the invention may be applied simultaneously (as a tank mix or a premix), separately or sequentially.

Thus, in accordance with the method of invention a synergistically effective amount of a combination of glyphosate and an imidazolinone compound selected from the group consisting of imazethapyr, imazaquin, imazapic, imazamox and imazapyr is applied to the locus, foliage or stems of undesirable plants, particularly plants selected from the genera Ipomoea, Cyperus, Sida and Euphorbia, preferably *Ipomoea lacunosa, Cyperus rotundus, Sida spinosa* and *Euphorbia maculata,* more preferably *Ipomoea lacunosa.*

Preferred combinations for the method of the invention are those combinations wherein the weight/weight (wt/wt) ratio of glyphosate:imidazolinone compound is about 3:1 to 65:1. More preferred combinations of the invention are combinations of glyphosate and imazethapyr wherein the wt/wt ratio of glyphosate:imazethapyr is about 8:1 to 12:1 or combinations of glyphosate and imazaquin wherein the wt/wt ratio of glyphosate:imazaquin is about 3:1 to 10:1 or combinations of glyphosate and imazapic wherein the wt/wt ratio of glyphosate:imazapic is about 15:1 to 65:1 or combinations of glyphosate and imazamox wherein the wt/wt ratio of glyphosate:imazamox is about 20:1 to 65:1.

The synergistically effective amount of the combination of glyphosate and an imidazolinone compound selected from imazethapyr, imazaquin, imazapic, imazamox and imazapyr may vary according to prevailing conditions such as the particular imidazolinone compound present, weed pressure, application timing, weather conditions, soil conditions, mode of application, topographical character, target crop species and the like. In general, a synergistic effect may be achieved at application rates of about 200 g/ha–800 g/ha of glyphosate in combination with about 8.0 g/ha–150 g/ha of an imidazolinone compound, preferably about 480 g/ha–720 g/ha of glyphosate in combination with about 60 g/ha–80 g/ha of imazethapyr.

In actual practice, a tank mix of a commercially convenient association or presentation of glyphosate and an imidazolinone compound selected from imazethapyr, imazaquin, imazapic, imazamox and imazapyr may be applied to the foliage of the crop, or the glyphosate and said imidazolinone compound may be applied separately or sequentially, or the combination compositions of the invention may be applied in a single combined form as described herein.

The synergistically effective amount of a combination of glyphosate and an imidazolinone compound suitable for use in the composition of the invention is that amount sufficient to provide about 200 g/ha–1200 g/ha of glyphosate and about 8.0 g/ha–150 g/ha of an imidazolinone compound, preferably about 400 g/ha–800 g/ha of glyphosate and about 55 g/ha–100 g/ha of imazethapyr, more preferably about 480 g/ha–720 g/ha of glyphosate and about 60 g/ha to 80 g/ha of imazethapyr.

The synergistic herbicidal compositions of the invention provide effective resistance management programs, including in crop production, for example glyphosate-resistant soybean, canola, sugarbeet, corn, wheat, rice and the like crop production, preferably glyphosate-resistant soybean crop production.

In a preferred embodiment of this invention, storage stable herbicidal compositions of this invention comprise about 0.1% w/v to about 7% w/v of an imidazolinyl acid salt, about 10% w/v to about 45% w/v of a glyphosate salt, about 0.5% w/v to about 6% w/v of dimethyl sulfoxide, about 0.5% w/v to about 15% w/v of a wetting agent, up to about 10% w/v of an antifreezing agent, up to about 1% w/v of an antifoaming agent, up to about 5% w/v of a base, and water, provided that the composition has an initial pH of from about 6.0 to about 7.2.

In a more preferred embodiment of the present invention, storage stable herbicidal compositions of this invention comprise about 0.1% w/v to about 7% w/v of an imidazolinyl acid salt, about 15% w/v to about 45% w/v of a glyphosate salt, about 0.5% w/v to about 6% w/v of dimethyl sulfoxide, about 0.5% w/v to about 15% w/v of a wetting agent, up to about 10% w/v of an antifreezing agent, up to about 1% w/v of an antifoaming agent, up to about 3% w/v of a base, and water, provided that the composition has an initial pH of from about 6.0 to about 7.0.

In another more preferred embodiment of the present invention, the aqueous herbicidal compositions comprise about 0.5% w/v to about 5% w/v of an imidazolinyl acid salt, about 20% w/v to about 35% w/v of a glyphosate salt, about 0.5% w/v to about 4% w/v of dimethyl sulfoxide, about 1% w/v to about 15% w/v of a wetting agent, about 1% w/v to about 5% w/v of an antifreezing agent, up to about 0.5% w/v of an antifoaming agent, up to about 2.5% w/v of a base, and water, provided that the composition has an initial pH of from about 6.0 to about 6.8.

Advantageously, it has been found that the compositions of the present invention provide physically and chemically stable concentrated, aqueous herbicidal compositions of imidazolinyl acid salts and glyphosate salts. The stability of the compositions of this invention is achieved by including dimethyl sulfoxide in the compositions and limiting the initial pH of the compositions to a pH value of from about 6.0 to about 7.2, preferably from about 6.0 to about 7.0. Beneficially, the compositions of this invention overcome the incompatibility problems associated with imidazolinyl acid salts and glyphosate salts without requiring the use of heavy aromatic solvents.

Imidazolinyl acid salts suitable for use in the stable compositions of this invention have the structural formula I

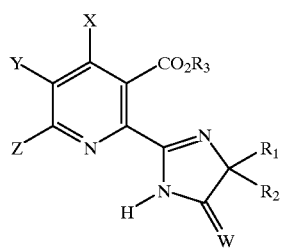

(I)

wherein

W is oxygen or sulfur;

$R_1$ is $C_1$–$C_4$alkyl;

$R_2$ is $C_1$–$C_4$alkyl or $C_3$–$C_6$cycloalkyl; and when $R_1$ and $R_2$ are taken together with the carbon to which they are attached they may represent $C_3$–$C_6$cycloalkyl optionally substituted with methyl;

X is hydrogen, halogen, hydroxyl or methyl;

Y and Z are independently hydrogen, halogen, $C_1$–$C_6$alkyl, $C_1$–$C_4$alkoxymethyl, hydroxyloweralkyl, $C_1$–$C_6$alkoxy, $C_1$–$C_4$alkylthio, phenoxy, $C_1$–$C_4$haloalkyl, nitro, cyano, $C_1$–$C_4$alkylamino, diloweralkylamino, or $C_1$–$C_4$alkyl-sulfonyl or phenyl optionally substituted with $C_1$–$C_4$alkyl, $C_1$–$C_4$alkoxy or halogen, and when taken together, Y and Z may form a ring in which YZ are represented by the structure: —$(CH_2)_n$—, where n is an integer of 3 or 4, provided that X is hydrogen, or

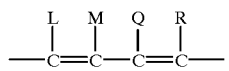

where L, M, Q and R are independently hydrogen, halogen, $C_1$–$C_4$alkyl or $C_1$–$C_4$alkoxy; and $R_3$ is an ammonium, organic ammonium, trialkylsulfonium or alkali metal cation.

The term loweralkyl means $C_1$–$C_6$alkyl, preferably $C_1$–$C_4$alkyl.

Preferred imidazolinyl acid salts for use in the compositions of this invention include:

salts of imazethapyr or its R isomer;

salts of imazaquin or its R isomer;

salts of imazapic or its R isomer;

salts of imazamox or its R isomer;

salts of imazapyr or its R isomer; and mixtures thereof.

Glyphosate salts suitable for use in the compositions of the present invention include, but are not limited to, glyphosate salts wherein the cation portion of the salt is an ammonium, organic ammonium, trialkylsulfonium or alkali metal cation. Preferred glyphosate salts are glyphosate organic amine salts such as $C_1$–$C_6$alkylamine salts, di-($C_1$–$C_6$alkyl)-amine salts and tri-($C_1$–$C_6$alkyl)-amine salts with $C_1$–$C_6$alkylamine salts being more preferred. Glyphosate isopropylamine salt is especially suitable for use in the compositons of this invention.

In another preferred embodiment of the present invention, the cation portion of the imidazolinyl acid salt and the glyphosate salt are the same. In particular, it has been found that compositions comprising imazethapyr isopropylamine salt and glyphosate isopropylamine salt are physically and chemically stable.

In order to provide herbicidally effective amounts of the co-active ingredients, the ratio of the imidazolinyl acid salt to the glyphosate salt in the compositions of this invention is preferably about 1:4 to about 1:15, more preferably about 1:7 to about 1:12, on a weight to volume basis.

Wetting agents suitable for use in the compositions of this invention include, but are not limited to, conventional wetting agents such as ethoxylated tallow amines, alpha olefin sulfonate salts, alkylphenol polyethylene oxide condensates and the like and mixtures thereof. Preferred wetting agents include ethoxylated tallow amines having 15 moles of ethylene oxide per molecule (such as SURFOM 5204-CS available from Oxiteno, Maua, Sao Paulo, Brazil; TOXIMUL® TA-15 available from Stepan Co., Northfield, Ill. and TOXIMUL®8362 available from Stepan Co.); sodium alpha olefin sulfonates (such as Witconate AOK available from Witco, Sao Paulo, Sao Paulo, Brazil); and nonylphenol ethoxylates (such as FLO MO®9N, available from Witco, New York, N.Y., United States);

and mixtures thereof Ethoxylated tallow amines are especially suitable for use in the stable compositions of this invention.

Antifreezing agents suitable for use in the compositions of the present invention include, but are not limited to, glycols such as propylene glycol and ethylene glycol, N-methylpyrrolidone, cyclohexanone, and alcohols such as ethanol and methanol. Preferred antifreezing agents include glycols with propylene glycol being an especially preferred antifreezing agent. Antifoaming agents suitable for use in this invention are conventional antifoaming agents including, but not limited to, silicone based antifoaming agents such as antifoam SE 47 (available from Wacker, Santo Amaro, Sao Paulo, Brazil).

In addition, the compositions of this invention may contain conventional additives used in aqueous compositions such as antimicrobial agents, antioxidants, buffers (including a $K_2HPO_4$/$KH_2PO_4$ mixture), dyes and the like and mixtures thereof.

A more preferred concentrated, aqueous herbicidal composition of this invention comprises about 2% w/v to about 4% w/v of imazethapyr isopropylamine salt, about 20% w/v to about 35% w/v of glyphosate isopropylamine salt, about 0.5% w/v to about 4% w/v of dimethyl sulfoxide, about 5% w/v to about 15% w/v of an ethoxylated tallow amine, about 1% w/v to about 5% w/v of propylene glycol, about 0.001% w/v to about 0.1% w/v of an antifoaming agent, about 0.5% w/v to about 2.5% w/v of a base, and water, provided that the composition has an initial pH of from about 6.0 to about 6.8 and the ratio of the imazethapyr isopropylamine salt to the glyphosate isopropylamine salt is about 1:7 to about 1:12.

Another more preferred concentrated, aqueous herbicidal composition of this invention comprises about 2% w/v to about 4% w/v of imazethapyr isopropylamine salt, about 15% w/v to about 18% w/v of glyphosate isopropylamine salt, about 0.5% w/v to about 4% w/v of dimethyl sulfoxide, about 5% w/v to about 15% w/v of an ethoxylated tallow amine, about 1% w/v to about 5% w/v of propylene glycol, about 0.001% w/v to about 0.1% w/v of an antifoaming agent, about 0.5% w/v to about 4% w/v of a base, and water, provided that the composition has an initial pH of from about 6.2 to about 6.5 and the ratio of the imazethapyr isopropylamine salt to the glyphosate isopropylamine salt is about 1:12.

Another more preferred concentrated, aqueous herbicidal composition of this invention comprises about 2% w/v to about 4% w/v of imazaquin isopropylamine salt, about 10% w/v to about 12% w/v of glyphosate isopropylamine salt, about 0.5% w/v to about 4% w/v of dimethyl sulfoxide, about 5% w/v to about 15% w/v of an ethoxylated tallow amine, about 1% w/v to about 5% w/v of propylene glycol, about 0.001% w/v to about 0.1% w/v of an antifoaming agent, about 0.5% w/v to about 4% w/v of a base, and water, provided that the composition has an initial pH of from about 7.0 to about 7.2 and the ratio of the imazaquin isopropylamine salt to the glyphosate isopropylamine salt is about 1:5.

The present invention also relates to a process for the preparation of concentrated, aqueous herbicidal compositions. The process of this invention comprises:

(a) providing a first aqueous solution containing an imidazolinyl acid salt;

(b) dispersing into the first aqueous solution, dimethyl sulfoxide and optionally an antifreezing agent to produce a second aqueous solution;

(c) adding into the second aqueous solution, an aqueous solution of a glyphosate salt to produce a homogeneous solution while maintaining the pH above about pH 6.0 with a base;

(d) adjusting the pH of the homogeneous solution produced in step (c) to about pH 6.0 to about 7.2, preferably about pH 6.0 to about 7.0, if necessary;

(e) adding into the pH adjusted solution obtained in step (d), a wetting agent and optionally an antifoaming agent; and (f) adding water.

Bases suitable for maintaining the pH of the solution produced in step (c) above about pH 6.0 include, but are not limited to, ammonia and organic amines and the like and mixtures thereof. Preferred bases include organic amines such as isopropylamine.

In a preferred process of the present invention, the pH is adjusted in step (d) with an acid. Acids suitable for use in the process of this invention include mineral acids and organic acids with organic acids such as acetic acid being preferred.

The concentrated, aqueous herbicidal compositions of this invention are diluted with water and applied as dilute, aqueous sprays to the locus where weed control is desired. While the compositions of this invention are effective for controlling weeds when employed alone, they may also be used in combination with other biological chemicals, including other herbicides.

For a more clear understanding of the invention, specific examples thereof are set forth below. These examples are merely illustrative, and are not to be understood as limiting the scope and underlying principles of the invention in any way.

In the following examples, synergism is determined by the Colby[1] method, i.e. the expected (or predicted) response of the combination is calculated by taking the product of the observed response for each individual component of the combination when applied alone divided by 100 and subtracting this value from the sum of the observed response for each component when applied alone. Synergism of the combination is then determined by comparing the observed response of the combination to the expected (or predicted) response as calculated from the observed responses of each individual component alone. If the observed response of the combination is significantly greater than the expected (or predicted) response as determined by Fisher's protected Least Significant Difference (LSD) test using significance level 0.05, than the combination is said to be synergistic.

[1]Colby, S.R., Weeds, 1967(15), p. 20–22

The foregoing is illustrated mathematically below, wherein a combination, C, is composed of component A plus component B and Obs. designates the observed response of the combination C.

$$(A+B) - \frac{AB}{100} = \text{Expected response (Exp.)}$$

$$\text{Synergism} \equiv (Obs.-\text{Exp.}) > LSD$$

EXAMPLE 1

Evaluation of the Herbicidal Activity of a Combination of Glyphosate and Imazethapyr In this evaluation, pitted morning glory plants (*Ipomoea lacunosa*) are grown in standard greenhouse soil until they have reached the 6-leaf stage. Said plants are then sprayed with an aqueous solution of the test compound using a spray nozzle operating at 30 psi for a predetermined time so as to obtain a range of application rates of about 20 g/ha to 720 g/ha. Each treatment is replicated 3 times. After spraying, the plants are placed on greenhouse benches and are cared for in a manner commensurate with standard greenhouse practice. At 4 weeks after treatment, the plants are examined, and the % weed control as compared to the untreated check is recorded. Also at 4 weeks after treatment, the plant height is measured and recorded as % height reduction as compared to the height of the untreated check. Plant heights are measured by stretching out the vines and measuring from the soil surface to the tip of the vine.

The data obtained are analyzed using conventional statistical analysis techniques to determine the least significant difference (LSD) or standard deviation. The Colby method of analysis is used to determine the resultant biological effect of the combination treatment as compared to the biological effect of each component of the combination when applied alone.

| TEST COMPOUNDS | SOURCE |
| --- | --- |
| Glyphosate, isopropylammonium salt 4AS | ROUNDUP ®[1] |
| Imazethapyr 100AS | PIVOT ® H[2] |

[1]manufactured by Monsanto
[2]manufactured by American Cyanamid Co.

TABLE I

Evaluation of Weed Control

| Glyphosate | Imazethapyr | % Weed Control | | |
|---|---|---|---|---|
| g/ha | g/ha | Observed | Expected | (Obs. -Exp.)[1] |
| 0 | 0 | 0.00 | — | |
| 0 | 60 | 3.33 | — | |
| 0 | 80 | 0.00 | — | |
| 0 | 100 | 30.00 | — | |
| 480 | 0 | 3.33 | — | |
| 720 | 0 | 23.33 | — | |
| 480 | 60 | 82.67 | 6.67 | 7.00* |
| 480 | 80 | 86.00 | 3.33 | 8.67* |
| 480 | 100 | 84.33 | 42.00 | 4.33* |
| 720 | 60 | 85.00 | 26.00 | 5.00* |
| 720 | 80 | 86.67 | 23.33 | 63.33* |
| 720 | 100 | 88.33 | 54.00 | 34.33* |

[1]LSD (0.05) = 17.4
*Synergistic, i.e. (obs.-exp.)>LSD

As can be seen from the data shown in Table I, application of a combination of glyphosate plus imazethapyr gave significantly greater weed control than that which could be predicted from the weed control resulting from the application of either imazethapyr alone or glyphosate alone.

TABLE II

Evaluation of Plant Height Reduction

| Glyphosate | Imaze-thapyr | Height | Height Reduction | | |
|---|---|---|---|---|---|
| g/ha | g/ha | (cm) | Observed | Expected | (Obs.-Exp.)[1] |
| 0 | 0 | 169 | 0.00 | — | |
| 0 | 60 | 143 | 15.35 | — | |
| 0 | 80 | 143 | 15.37 | — | |
| 0 | 100 | 115 | 31.47 | — | |
| 480 | 0 | 141 | 16.75 | — | |
| 720 | 0 | 106 | 37.11 | — | |
| 480 | 60 | 61 | 63.49 | 29.75 | 33.74* |
| 480 | 80 | 60 | 64.58 | 29.58 | 5.00* |
| 480 | 100 | 59 | 64.87 | 43.71 | 21.16* |
| 720 | 60 | 62 | 63.55 | 46.40 | 17.15 |
| 720 | 80 | 53 | 68.70 | 46.64 | 22.06* |
| 720 | 100 | 52 | 68.94 | 55.81 | 13.14 |

[1]LSD (0.05) = 17.4
*Synergistic, i.e. (obs.-exp.)>LSD

As can be seen from the data shown in Table II application of a combination of glyphosate plus imazethapyr at 4 of the 6 rates tested gave significantly greater height reduction than that which could be predicted from the application of either glyphosate alone or imazethapyr alone.

EXAMPLE 2

Evaluation of the Herbicidal Actvity of a Combination of Glyphosate and Imazapic In this evaluation pitted morningglory plants (*Ipomoea lacunosa*) are grown in a 1:1 mixture of sandy loam soil and masonry sand until they have reached the 5-leaf stage. Said plants are then sprayed with an aqueous solution of test compound using a $CO_2$-pressurized spray chamber. Each treatment is replicated 4 times. After spraying, the plants are placed on greenhouse benches and cared for in a manner commensurate with conventional greenhouse practice. At 4 weeks after treatment the plants are visually examined and % weed control as compared to the untreated check is recorded. Also at 4 weeks after treatment, the number of leaves are counted and are recorded as % leaf reduction as compared to the untreated check. After the visual ratings, the plant is excised at the soil surface and the excised vegetation is weighed and measured. Plant fresh weight and height are recorded as % weight reduction as compared to untreated check and as % height reduction as compared to untreated check.

The data are analyzed using standard statistical analysis techniques to determine the least significant difference (LSD) or standard deviation. The Colby method is used to determine if the test combination demonstrates a synergistic interaction.

| TEST COMPOUNDS | SOURCE |
|---|---|
| Glyphosate, isopropylammonium salt | ROUNDUP ® ULTRA[1] |
| Imazapic | CADRE ®[2] |

[1]manufactured by Monsanto
[2]manufactured by American Cyanamid Co.

TABLE III

Evaluation of Weed Control

| Glyphosate | Imazapic | % Weed Control | | |
|---|---|---|---|---|
| g/ha | g/ha | Observed | Expected | (Obs.-Exp.)[1] |
| 0 | 0 | 0 | — | |
| 0 | 8.97 | 35.00 | — | |
| 0 | 13.45 | 28.75 | — | |
| 0 | 17.93 | 20.00 | — | |
| 280.2 | 0 | 23.75 | — | |
| 560.4 | 0 | 5.00 | — | |
| 280.2 | 8.97 | 51.25 | 50.38 | 0.88 |
| 280.2 | 13.45 | 73.75 | 45.81 | 27.94* |
| 280.2 | 17.93 | 77.50 | 39.00 | 38.50* |
| 560.4 | 8.97 | 55.00 | 38.25 | 16.75* |
| 560.4 | 13.45 | 78.75 | 32.31 | 46.44* |
| 560.4 | 17.93 | 86.25 | 24.00 | 62.25* |

[1]LSD (0.05) = 10.76
*Synergistic, i.e. (obs.-exp.)>LSD

TABLE IV

Evaluation of Leaf Reduction

| Gly-phosate | Imazapic | Number | % Leaf Reduction | | |
|---|---|---|---|---|---|
| g/ha | g/ha | of leaves | Observed | Expected | (Obs.-Exp.)[1] |
| 0 | 0 | 13.3 | 0 | — | |
| 0 | 8.97 | 8.8 | 26.34 | — | |
| 0 | 13.45 | 9.0 | 32.46 | — | |
| 0 | 17.93 | 6.0 | 50.89 | — | |
| 280.2 | 0 | 10.8 | 6.66 | — | |
| 560.4 | 0 | 12.5 | 0.17 | — | |
| 280.2 | 8.97 | 5.3 | 58.80 | 16.24 | 42.56* |
| 280.2 | 13.45 | 3.8 | 69.44 | 36.62 | 32.81* |
| 280.2 | 17.93 | 5.5 | 55.23 | 46.61 | 8.62 |
| 560.4 | 8.97 | 5.5 | 54.48 | 19.71 | 34.77* |
| 560.4 | 13.45 | 4.5 | 65.52 | 32.22 | 33.30* |
| 560.4 | 17.93 | 3.0 | 77.29 | 47.34 | 29.96* |

[1]LSD (0.05) = 23.28
*Synergistic, i.e. (obs.-exp.)>LSD

EXAMPLE 3
Evaluation of the Herbicidal Activity of a Combination of Glyphosate and Imazamox Using essentially the same procedure described in Example 2 hereinabove, 5-leaf pitted morningglory plants are treated with test compounds and evaluated at 3 weeks after treatment. Each treatment is replicated 4 times. The data are averaged and shown in Tables V and VI below.

| TEST COMPOUND | SOURCE |
|---|---|
| Glyphosate, isopropylammonium salt | ROUNDUP ® ULTRA[1] |
| Imazamox | RAPTOR ®[2] |

[1] manufactured by Monsanto
[2] manufactured by American Cyanamid Co.

TABLE V

Evaluation of Weed Control

| Glyphosate | Imazamox | | % Weed Control | |
|---|---|---|---|---|
| g/ha | g/ha | Observed | Expected | Obs.-Exp.)[1] |
| 0 | 0 | 0 | — | |
| 0 | 8.97 | 5.00 | — | |
| 0 | 17.93 | 32.50 | — | |
| 0 | 26.90 | 66.25 | — | |
| 560.4 | 0 | 7.50 | — | |
| 560.4 | 8.97 | 45.00 | 12.13 | 32.88* |
| 560.4 | 17.93 | 78.75 | 37.63 | 41.13* |
| 560.4 | 26.90 | 78.75 | 68.81 | 9.94 |

[1] LSD (0.05) = 15.55
*Synergistic, i.e. (obs.-exp.)>LSD

TABLE VI

Evaluation of Fresh Weight Reduction

| Glyphosate | Imazanox | Weight | | % Weight Reduction | |
|---|---|---|---|---|---|
| g/ha | g/ha | (g) | Observed | Expected | (Obs.-Exp.)[1] |
| 0 | 0 | 4.38 | 0 | — | |
| 0 | 8.97 | 4.19 | 4.19 | — | |
| 0 | 17.93 | 4.49 | -4.55 | — | |
| 0 | 26.90 | 3.02 | 30.41 | — | |
| 560.4 | 0 | 5.22 | -22.39 | — | |
| 560.4 | 8.97 | 3.61 | 14.02 | -17.06 | 31.08 |
| 560.4 | 17.93 | 2.82 | 32.80 | -31.26 | 54.06* |
| 560.4 | 26.90 | 2.30 | 47.16 | -13.86 | 33.30 |

[1] LSD (0.05) = 35.34
*Synergistic, i.e. (obs.-exp.)>LSD

TABLE VII

Evaluation of Leaf Reduction

| Glyphosate | Imazamox | Number | | % Leaf Reduction | |
|---|---|---|---|---|---|
| g/ha | g/ha | of Leaves | Observed | Expected | (Obs.-Exp.)[1] |
| 0 | 0 | 21.75 | 0 | — | |
| 0 | 8.97 | 17.50 | 15.00 | — | |
| 0 | 17.93 | 11.00 | 47.98 | — | |
| 0 | 26.90 | 7.00 | 66.21 | — | |
| 560.4 | 0 | 23.00 | -16.18 | — | |
| 560.4 | 8.97 | 9.25 | 56.33 | -8.80 | 65.13* |
| 560.4 | 17.93 | 7.25 | 64.17 | 37.47 | 26.70* |
| 560.4 | 26.90 | 6.50 | 67.93 | 57.22 | 10.71 |

[1] LSD (0.05) = 21.86
*Synergistic, i.e. (obs.-exp.)>LSD

EXAMPLE 4

Evaluation of the Herbicidal Activity of a Combination of Glyphosate and the R Isomer of an Imidazolinone Compound In this evaluation pitted morningglory (*Ipomoea lacunosa*) and purple nutsedge (*Cyperus rotundus*) plants are grown in a 1:1 mixture of fine sandy loam soil and masonry sand to the 5–7 leaf stage for the pitted morningglory plants and the 10–15 leaf stage for the purple nutsedge plants. Said plants are then sprayed with an aqueous solution of test compound using a $CO_2$-pressurized spray chamber at a volume of 15 gallons/acre. Each treatment is replicated 4 times. After spraying, the plants are placed on greenhouse benches and cared for in a manner commensurate with conventional greenhouse practice. At regular intervals, plants are visually examined and % weed control as compared to the untreated check is recorded. The data are analyzed using standard statistical techniques to determine the least significant difference (LDS) or standard deviation. The Colby method is used to determine if the test combination demonstrates a synergistic interaction.

| Test Compounds | | |
|---|---|---|
| Glyphosate, isopropylamonnium salt (ROUNDUP ® ULTRA)[1] | | |
| Compound A | = | R isomer of imazapyr[2] |
| Compound B | = | R isomer of imazapic[2] |
| Compound C | = | R isomer of imazamox[2] |
| Compound D | = | R isomer of imazethapyr[2] |

[1] Manufactured by Monsanto
[2] Formulated as an aqueous concentrate according to US 4,816,060
[2] Formulated as an aqueous concentrate according to U.S. Pat. No. 4,816,060

TABLE VIII

Evaluation of Control of Pitted Morningglory At 5 Weeks After Treatment

| Gly-phosate | Imidazolinone | | % Weed Control | | |
|---|---|---|---|---|---|
| (g/ha) | Cmpd | (g/ha) | Observed | Expected | (Obs.-Exp.)[1] |
| 0 | | 0 | 0 | — | |
| 0 | A | 5.6 | 47.50 | — | |
| 0 | B | 9.0 | 22.50 | — | |
| 0 | C | 12.3 | 22.50 | — | |
| 0 | D | 23.5 | 22.50 | — | |
| 560 | | 0 | 3.75 | — | |
| 560 | A | 5.6 | 71.25 | 49.50 | 21.75* |
| 560 | B | 9.0 | 67.50 | 25.50 | 42.00* |
| 560 | C | 12.3 | 75.00 | 25.38 | 49.63* |
| 560 | D | 23.5 | 71.25 | 25.50 | 45.75* |

[1] LSD = 12.6
*Synergistic, i.e. (obs.-exp.)>LSD

TABLE IX

Evaluation of Control of Purple Nutsedge At 4 Weeks After Treatment

| Gly-phosate | Imidazolinone | | % Weed Control | | |
|---|---|---|---|---|---|
| (g/ha) | Cmpd | (g/ha) | Observed | Expected | (Obs.-Exp.)[1] |
| 0 | | 0 | 0 | — | |
| 0 | A | 5.6 | 0 | — | |

TABLE IX-continued

Evaluation of Control of Purple Nutsedge
At 4 Weeks After Treatment

| Gly-phosate (g/ha) | Imidazolinone Cmpd | (g/ha) | % Weed Control Observed | Expected | (Obs.-Exp.)[1] |
|---|---|---|---|---|---|
| 0 | B | 9.0 | 0 | — | |
| 0 | C | 12.3 | 0 | — | |
| 0 | D | 23.5 | 0 | — | |
| 560 | | 0 | 15.00 | — | |
| 560 | A | 5.6 | 38.33 | 15.00 | 23.33* |
| 560 | B | 9.0 | 40.00 | 15.00 | 5.00* |
| 560 | C | 12.3 | 38.33 | 15.00 | 23.33* |
| 560 | D | 23.5 | 60.00 | 15.00 | 5.00* |

[1]LSD = 9.7
*Synergistic, i.e. (obs.-exp.)>LSD (2) add dimethyl sulfoxide and optionally propylene glycol to the first aqueous solution to obtain a second aqueous solution;

(3) add an aqueous solution of glyphosate isopropylamine salt to the second aqueous solution to obtain a homogeneous solution while maintaining the pH above about pH 6.2 with a base;

(4) adjust the pH of the homogeneous solution to a pH value of about pH 6.2 to about pH 6.8 with a 10% w/w acetic acid solution;

(5) add SURFOM 5204-CS (ethoxylated tallow amine wetting agent) and antifoam SE 47 (antifoaming agent) to the pH-adjusted solution; and (6) add water.

TABLE X

Concentrated, Aqueous Herbicidal Compositions
Ingredient/% w/v

| Comp. No. | Imaz-ethapyr IPA salt | Glypho-sate IPA salt | DMSO | Propylene Glycol | Base[1] | SURFOM 5204-CS | Anti-foam SE 47 | Acetic Acid | $K_2HPO_4$ | $KH_2PO_4$ | Water | pH |
|---|---|---|---|---|---|---|---|---|---|---|---|---|
| 1 | 2.70 | 32.40 | 1.35 | 3.00 | a/0.81 | 15.66 | 0.01 | 0.16 | — | — | to 100 | 6.1 |
| 2 | 2.50 | 30.00 | 1.25 | 3.00 | a/0.75 | 14.50 | 0.01 | 0.15 | — | — | to 100 | 6.1 |
| 3 | 2.00 | 24.00 | 1.00 | 3.00 | a/0.80 | 11.80 | 0.01 | 0.12 | — | — | to 100 | 6.0 |
| 4 | 2.50 | 30.00 | 1.25 | 3.00 | a/0.75 | 14.50 | 0.01 | — | — | — | to 100 | 6.2 |
| 5 | 3.50 | 28.00 | 1.75 | 3.00 | a/1.06 | 13.53 | 0.01 | 0.21 | — | — | to 100 | 6.1 |
| 6 | 3.00 | 24.00 | 1.50 | 3.00 | a/0.90 | 11.80 | 0.01 | 0.18 | — | — | to 100 | 6.1 |
| 7 | 3.50 | 28.00 | 1.75 | 3.50 | a/1.06 | 13.53 | 0.01 | — | — | — | to 100 | 6.2 |
| 8 | 3.00 | 21.00 | 1.50 | 3.00 | b/1.50 | 10.15 | 0.01 | 0.12 | 0.05 | 0.02 | to 100 | 6.2 |
| 9 | 3.00 | 21.00 | 1.50 | 3.00 | a/0.78 | 10.15 | 0.01 | 0.07 | 0.05 | 0.02 | to 100 | 6.1 |
| 10 | 4.00 | 28.00 | 2.00 | 3.00 | b/2.00 | 13.63 | 0.01 | 0.01 | 0.02 | 0.07 | to 100 | 6.2 |
| 11 | 4.00 | 28.00 | 2.00 | 3.00 | a/1.04 | 13.53 | 0.01 | 0.01 | 0.02 | 0.07 | to 100 | 6.4 |
| 12 | 3.00 | 21.00 | 2.00 | 3.00 | a/0.90 | 10.15 | 0.01 | 0.18 | — | — | to 100 | 6.7 |
| 13 | 4.00 | 28.00 | 2.00 | 3.00 | a/1.20 | 13.53 | 0.01 | 0.24 | — | — | to 100 | 6.7 |
| 14 | 4.00 | 28.00 | 2.00 | 3.00 | a/1.20 | 13.53 | 0.01 | 0.24 | — | — | to 100 | 6.4 |
| 15 | 3.00 | 21.00 | 2.00 | 3.00 | a/0.90 | 10.15 | 0.01 | 0.18 | — | — | to 100 | 6.4 |
| 16 | 3.00 | 21.00 | 1.50 | 3.00 | a/0.90 | 10.15 | 0.01 | 0.18 | — | — | to 100 | 6.1 |
| 17 | 4.00 | 28.00 | 2.00 | 3.00 | a/1.90 | 13.53 | 0.01 | 0.24 | — | — | to 100 | 6.2 |
| 18 | 4.00 | 28.00 | 3.50 | 1.60 | a/1.20 | 13.53 | 0.01 | 0.24 | — | — | to 100 | 6.1 |
| 19 | 4.00 | 28.00 | 3.50 | — | a/1.20 | 13.53 | 0.01 | 0.24 | — | — | to 100 | 6.1 |
| 20 | 4.00 | 28.00 | 2.00 | 1.50 | a/1.20 | 13.53 | 0.01 | 0.24 | — | — | to 100 | 6.2 |
| 21 | 4.00 | 28.00 | 2.00 | 3.00 | a/1.20 | 13.53 | 0.01 | 0.24 | — | — | to 100 | 6.2 |
| 22 | 4.00 | 28.00 | 2.00 | — | a/1.20 | 13.53 | 0.01 | 0.24 | — | — | to 100 | 6.2 |
| 23 | 3.70 | 26.00 | 0.80 | — | b/1.92 | 12.55 | 0.01 | 0.18 | — | — | to 100 | 6.1 |
| 24 | 3.70 | 26.00 | 0.80 | — | b/1.92 | 12.55 | 0.01 | 0.18 | — | — | to 100 | 6.1 |
| 25 | 4.00 | 28.00 | 1.00 | — | b/2.06 | 13.53 | 0.01 | 0.24 | — | — | to 100 | 6.1 | a. isopropylamine
b. ammonia

EXAMPLE 5

Preparation of Concentrated, Aqueous Herbicidal Compositions Containing Imazethapyr Isopropylamine Salt and Glyphosate Isopropylamine Salt The concentrated, aqueous herbicidal compositions identified below in Table X are prepared according to the following generic procedure:

(1) prepare a first aqueous solution of imazethapyr isopropylamine salt from imazethapyr and isopropylamine;

EXAMPLE 6

Evaluation of the Storage Stability of Concentrated, Aqueous Herbicidal Compositions The storage stability of the concentrated, aqueous herbicidal compositions prepared in Example 5 are evaluated by storing samples of the compositions at room temperature (RT), 45° C. and 5° C. The samples are removed periodically and visually inspected for physical changes in the appearance of the compositions. The results are summarized in Table XI. As can be seen from the data in Table XI, the compositions of the present invention are especially stable for prolonged periods of time when stored above 5° C.

TABLE XI

Storage Stability of Concentrated, Aqueous Herbicidal Compositions

| Comp. Number | Storage Temperature | Storage Period | | | | | |
|---|---|---|---|---|---|---|---|
| | | 1 week | 2 weeks | 3 weeks | 1 month | 2 months | 3 months |
| 1 | RT | no change | no change | no change | no change | no change | no change |
| | 45° C. | no change | no change | no change | no change | no change | no change |
| | 5° C. | no change | no change | no change | no change | no change | no change |
| 2 | RT | no change | no change | no change | no change | no change | no change |
| | 45° C. | no change | no change | no change | no change | no change | no change |
| | 5° C. | no change | no change | no change | no change | no change | no change |
| 3 | RT | no change | no change | no change | no change | no change | no change |
| | 45° C. | no change | no change | no change | no change | no change | no change |
| | 5° C. | no change | no change | no change | no change | no change | no change |
| 4 | RT | — | — | — | — | — | no change |
| | 45° C. | — | — | — | — | — | no change |
| | 5° C. | — | — | — | — | — | crystal growth |
| 5 | RT | no change | no change | no change | no change | no change | no change |
| | 45° C. | no change | no change | no change | no change | no change | no change |
| | 5° C. | no change | no change | no change | no change | no change | no change |
| 6 | RT | — | — | — | — | — | no change |
| | 45° C. | — | — | — | — | — | no change |
| | 5° C. | — | — | — | — | — | crystal growth |
| 7 | RT | no change | no change | no change | no change | no change | no change |
| | 45° C. | no change | no change | no change | no change | no change | no change |
| | 5° C. | no change | no change | no change | no change | no change | no change |
| 8 | RT | no change | no change | no change | no change | no change | no change |
| | 45° C. | no change | no change | no change | no change | no change | no change |
| | 5° C. | no change | no change | no change | no change | no change | no change |
| 9 | RT | no change | no change | no change | no change | no change | no change |
| | 45° C. | no change | no change | no change | no change | no change | no change |
| | 5° C. | no change | no change | no change | no change | no change | no change |
| 10 | RT | no change | no change | no change | no change | no change | no change |
| | 45° C. | no change | no change | no change | no change | no change | no change |
| | 5° C. | no change | no change | no change | no change | — | — |
| 11 | RT | no change | no change | no change | no change | no change | no change |
| | 45° C. | no change | no change | no change | no change | no change | no change |
| | 5° C. | no change | no change | no change | no change | — | — |
| 12 | RT | no change | no change | no change | no change | no change | no change |
| | 45° C. | no change | no change | no change | no change | no change | no change |
| | 5° C. | no change | no change | no change | no change | no change | no change |
| 13 | RT | no change | no change | no change | no change | no change | no change |
| | 45° C. | no change | no change | separation | separation | separation | no change |
| | 5° C. | no change | no change | no change | no change | no change | no change |
| 14 | RT | no change | no change | no change | no change | no change | no change |
| | 45° C. | no change | no change | no change | no change | no change | no change |
| | 5° C. | no change | no change | no change | no change | no change | no change |
| 15 | RT | no change | no change | no change | no change | no change | no change |
| | 45° C. | no change | no change | no change | no change | no change | no change |
| | 5° C. | no change | no change | no change | no change | no change | no change |
| 16 | RT | no change | no change | no change | no change | no change | no change |
| | 45° C. | no change | no change | no change | no change | no change | no change |
| | 5° C. | no change | no change | no change | no change | no change | no change |
| 17 | RT | no change | no change | no change | no change | no change | no change |
| | 45° C. | no change | no change | no change | no change | no change | no change |
| | 5° C. | no change | no change | no change | no change | no change | no change |
| 18 | RT | no change | no change | no change | no change | no change | no change |
| | 45° C. | no change | no change | no change | no change | no change | no change |
| | 5° C. | no change | no change | crystal growth | crystal growth | crystal growth | crystal growth |
| 19 | RT | no change | no change | no change | no change | no change | no change |
| | 45° C. | no change | no change | no change | no change | no change | no change |
| | 5° C. | no change | crystal growth | crystal growth | crystal growth | crystal growth | crystal growth |
| 20 | RT | no change | no change | no change | trace crystal growth | trace crystal growth | trace crystal growth |
| | 45° C. | no change | no change | no change | no change | — | no change |
| | 5° C. | no change | crystal growth | crystal growth | crystal growth | crystal growth | crystal growth |
| 21 | RT | no change | no change | no change | trace crystal growth | trace crystal growth | trace crystal growth |
| | 45° C. | no change | no change | no change | no change | no change | no change |
| | 5° C. | no change | crystal growth | crystal growth | crystal growth | crystal growth | crystal growth |
| 22 | RT | no change | no change | no change | trace crystal growth | trace crystal growth | trace crystal growth |
| | 45° C. | no change | no change | no change | no change | no change | no change |
| | 5° C. | no change | crystal growth | crystal growth | crystal growth | crystal growth | crystal growth |
| 23 | RT | no change | no change | no change | trace crystal growth | crystal growth | trace crystal growth |
| | 45° C. | no change | no change | no change | no change | no change | no change |
| | 5° C. | crystal growth | crystal growth | crystal growth | crystal growth | — | |

TABLE XI-continued

Storage Stability of Concentrated, Aqueous Herbicidal Compositions

| Comp. Number | Storage Temperature | Storage Period | | | | | |
|---|---|---|---|---|---|---|---|
| | | 1 week | 2 weeks | 3 weeks | 1 month | 2 months | 3 months |
| 24 | RT | no change | no change | no change | trace crystal growth | crystal growth | trace crystal growth |
| | 45° C. | no change | no change | no change | no change | no change | no change |
| | 5° C. | no change | crystal growth | crystal growth | crystal growth | — | — |
| 25 | RT | no change | crystal growth | crystal growth | crystal growth | crystal growth | crystal growth |
| | 45° C. | no change | no change | no change | no change | no change | no change |
| | 5° C. | crystal growth | crystal growth | crystal growth | — | — | — |

EXAMPLE 7

Comparative Evaluations of the Storage Stability of Concentrated, Aqueous Herbicidal Compositions The storage stability of composition numbers 20, 21 and 22 from Example 5 are compared to comparative compositions A, B and C. Comparative compositions A, B and C are essentially identical to compositions 20, 21 and 22, respectively, except that compositions A, B and C each have an initial pH value of 5.8. The compositions are evaluated according to the procedure described in Example 6, and the results are summarized in Table XII.

As can be seen from the data in Table XII, the compositions of the present invention, which have an initial pH value of 6.2, are more storage stable than the comparative compositions which have an initial pH value of 5.8.

(1) prepare a first aqueous solution of imazaquin isopropylamine salt from imazaquin (274.5 g, 97%) and isopropylamine (316.4 g);

(2) add dimethyl sulfoxide (125.7 g) and propylene glycol (251.4 g) to the first aqueous solution to obtain a second aqueous solution;

(3) add an aqueous solution of glyphosate isopropylamine salt (2,059.8 g, 45.53%) to the second aqueous solution to obtain a homogeneous solution;

(4) add TOXIMUL® 8362 (418.9 g) and antifoam SE 21 (0.9 g) to the homogeneous solution;

(5) adjust the pH to about 7.0 to 7.2, if necessary; and (6) add water (5,482.4 g).

The density of the composition is 1.068 g/mL.

TABLE XII

| Composition Number | Initial pH | Storage Temperature | Storage Period | | | |
|---|---|---|---|---|---|---|
| | | | 1 week | 2 weeks | 3 weeks | 1 month |
| 20 | 6.2 | RT | no change | no change | no change | trace crystal growth |
| | 6.2 | 45° C. | no change | no change | no change | no change |
| | 6.2 | 5° C. | no change | crystal growth | crystal growth | crystal growth |
| A | 5.8 | RT | crystal growth | crystal growth | crystal growth | crystal growth |
| | 5.8 | 45° C. | no change | no change | no change | no change |
| | 5.8 | 5° C. | crystal growth | crystal growth | crystal growth | crystal growth |
| 21 | 6.2 | RT | no change | no change | no change | trace crystal growth |
| | 6.2 | 45° C. | no change | no change | no change | no change |
| | 6.2 | 5° C. | no change | crystal growth | crystal growth | crystal growth |
| B | 5.8 | RT | crystal growth | crystal growth | crystal growth | crystal growth |
| | 5.8 | 45° C. | no change | no change | no change | no change |
| | 5.8 | 5° C. | crystal growth | crystal growth | crystal growth | crystal growth |
| 22 | 6.2 | RT | no change | no change | no change | trace crystal growth |
| | 6.2 | 45° C. | no change | no change | no change | no change |
| | 6.2 | 5° C. | no change | crystal growth | crystal growth | crystal growth |
| C | 5.8 | RT | crystal growth | crystal growth | crystal growth | crystal growth |
| | 5.8 | 45° C. | no change | no change | no change | no change |
| | 5.8 | 5° C. | crystal growth | crystal growth | crystal growth | crystal growth |

EXAMPLE 8

Preparation of a Concentrated, Aqueous Herbicidal Composition Containing Imazaquin Isopropylamine Salt and Glyphosate Isopropylamine Salt in a 1:5 Ratio A concentrated, aqueous herbicidal composition containing 3.08% w/w imazaquin technical (97%); 23.11% w/w of a glyphosate isopropylamine solution (45.53%); 3.36% w/w isopropylamine; 1.41% w/w dimethyl sulfoxide; 2.82% w/w propylene glycol; 0.01% w/w antifoam SE 21, a silicone antifoam; 4.70% w/w TOXIMUL® 8362; and water is prepared according to the following procedure:

EXAMPLE 9

Preparation of a Concentrated, Aqueous Herbicidal Composition Containing Imazethapyr Isopropylamine Salt and Glyphosate Isopropylamine Salt in a 1:12 Ratio A concentrated, aqueous herbicidal composition containing 1.97% w/w imazethapyr technical (98.37%); 35.76% w/w of a glyphosate isopropylamine solution (45.53%); 3.22% w/w isopropylamine; 0.88% w/w dimethyl sulfoxide; 2.75% w/w propylene glycol; 0.01% w/w antifoam SE 21, a silicone antifoam; 6.10% w/w TOXIMUL® 8362; and water is prepared according to the following procedure:

(1) prepare a first aqueous solution of imazethapyr isopropylamine salt from imazethapyr (180.2 g, 98.37%) and isopropylamine (294.5 g);

(2) add dimethyl sulfoxide (80.5 g) and propylene glycol (251.5 g) to the first aqueous solution to obtain a second aqueous solution;

(3) add an aqueous solution of glyphosate isopropylamine salt (3,270.6 g, 45.53%) to the second aqueous solution to obtain a homogeneous solution;

(4) add TOXIMUL® 8362 (557.9 g) and antifoam SE 21 (0.9 g) to the homogeneous solution;

(5) adjust the pH to about 6.2 to 6.5, if necessary; and (6) add water (4,509.9 g).

The density of the composition is 1.096 g/mL.

What is claimed is:

1. A method for the synergistic control of undesirable Ipomoea, Cyperus, Sida and Euphorbia plants which comprises applying to the locus of said plants or to the foliage or stems of said plants a synergistically effective amount of a combination of glyphosate and an imidazolinone compound selected from the group consisting of imazethapyr; imazapic; imazamox; imazapyr; and a mixture thereof.

2. The method according to claim 1 wherein said plants are Ipomoea or Cyperus.

3. The method according to claim 1 wherein the imidazolinone compound is selected from the group consisting of imazethapyr or the R isomer thereof; imazapic or the R isomer thereof; and imazamox or the R isomer thereof.

4. The method according to claim 1 wherein the glyphosate and imidazolinone compound are present at a wt/wt ratio of about 3:1 to 65:1.

5. The method according to claim 1 wherein the synergistically effective amount is about 200 g/ha–1200 g/ha of glyphosate and about 8.0 g/ha–150 g/ha of an imidazolinone compound.

6. A concentrated, aqueous, synergistic, herbicidal composition which comprises about 0.1% w/v to about 7% w/v of an imidazolinyl acid salt, about 10% w/v to about 45% w/v of a glyphosate salt, about 0.5% w/v to about 6% w/v of dimethyl sulfoxide, about 0.5% w/v to about 15% w/v of a wetting agent, up to about 10% w/v of an antifreezing agent, up to about 1% w/v of an antifoaming agent, up to about 5% w/v of a base, and water, provided that the composition has an initial pH of from about 6.0 to about 7.2.

7. The composition according to claim 6 which comprises about 0.1% w/v to about 7% w/v of an imidazolinyl acid salt, about 15% w/v to about 45% w/v of a glyphosate salt, about 0.5% w/v to about 6% w/v of dimethyl sulfoxide, about 0.5% w/v to about 15% w/v of a wetting agent, up to about 10% w/v of an antifreezing agent, up to about 1% w/v of an antifoaming agent, up to about 3% w/v of a base, and water, provided that the composition has an initial pH of from about 6.0 to about 7.0.

8. The composition according to claim 7 which comprises about 0.5% w/v to about 5% w/v of the imidazolinyl acid salt, about 20% w/v to about 35% w/v of the glyphosate salt, about 0.5% w/v to about 4% w/v of dimethyl sulfoxide, about 1% w/v to about 15% w/v of the wetting agent, about 1% w/v to about 5% w/v of the antifreezing agent, up to about 0.5% w/v of the anti-foaming agent, up to about 2.5% w/v of the base, and water, provided that the composition has an initial pH of from about 6.0 to about 6.8.

9. The composition according to claim 6 wherein the cation portion of the imidazolinyl acid salt and the glyphosate salt is an ammonium, organic ammonium, trialkylsulfonium or alkali metal cation.

10. The composition according to claim 6 wherein the imidazolinyl acid salt is selected from the group consisting of a salt of imazethapyr or its R isomer; a salt of imazamox or its R isomer; a salt of imazapic or its R isomer; a salt of imazapyr or its R isomer; and a salt of imazaquin or its R isomer.

11. The composition according to claim 6 which comprises about 2% w/v to about 4% w/v of imazethapyr isopropylamine salt, about 20% w/v to about 35% w/v of glyphosate isopropylamine salt, about 0.5% w/v to about 4% w/v of dimethyl sulfoxide, about 5% w/v to about 15% w/v of an ethoxylated tallow amine, about 1% w/v to about 5% w/v of propylene glycol, about 0.001% w/v to about 0.1% w/v of an antifoaming agent, about 0.5% w/v to about 2.5% w/v of a base, and water, provided that the composition has an initial pH of from about 6.0 to about 6.8 and the ratio of the imazethapyr isopropylamine salt to the glyphosate isopropylamine salt is about 1:7 to about 1:12.

12. The composition according to claim 6 which comprises about 2% w/v to about 4% w/v of imazethapyr isopropylamine salt, about 15% w/v to about 18% w/v of glyphosate isopropylamine salt, about 0.5% w/v to about 4% w/v of dimethyl sulfoxide, about 5% w/v to about 15% w/v of an ethoxylated tallow amine, about 1% w/v to about 5% w/v of propylene glycol, about 0.001% w/v to about 0.1% w/v of an antifoaming agent, about 0.5% w/v to about 4% w/v of a base, and water, provided that the composition has an initial pH of from about 6.2 to about 6.5 and the ratio of the imazethapyr isopropylamine salt to the glyphosate isopropylamine salt is about 1:12.

13. The composition according to claim 6 which comprises about 2% w/v to about 4% w/v of imazaquin isopropylamine salt, about 10% w/v to about 12% w/v of glyphosate isopropylamine salt, about 0.5% w/v to about 4% w/v of dimethyl sulfoxide, about 5% w/v to about 15% w/v of an ethoxylated tallow amine, about 1% w/v to about 5% w/v of propylene glycol, about 0.001% w/v to about 0.1% w/v of an antifoaming agent, about 0.5% w/v to about 4% w/v of a base, and water, provided that the composition has an initial pH of from about 7.0 to about 7.2 and the ratio of the imazaquin isopropylamine salt to the glyphosate isopropylamine salt is about 1:5.

14. A process for the preparation of a concentrated, aqueous herbicidal composition which process comprises:

(a) providing a first aqueous solution containing an imidazolinyl acid salt;

(b) dispersing into the first aqueous solution, dimethyl sulfoxide and optionally an antifreezing agent to produce a second aqueous solution;

(c) adding into the second aqueous solution, an aqueous solution of a glyphosate salt to produce a homogeneous solution while maintaining the pH above about pH 6.0 with a base;

(d) adjusting the pH of the homogeneous solution produced in step (c) to about pH 6.0 to about pH 7.2, if necessary;

(e) adding into the pH adjusted solution obtained in step (d), a wetting agent and optionally an antifoaming agent; and (f) adding water.

\* \* \* \* \*